United States Patent
Sinha et al.

(10) Patent No.: US 12,293,648 B2
(45) Date of Patent: *May 6, 2025

(54) SYSTEMS AND METHOD FOR CLOSED LOOP TRACKING OF HAND HYGIENE COMPLIANCE

(71) Applicant: Kohler Co., Kohler, WI (US)

(72) Inventors: Sudhi R. Sinha, Mumbai (IN); Orkun Onur, Greenville, SC (US); Andrew Baines, Cheltenham (GB)

(73) Assignee: Kohler Co., Kohler, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/221,536

(22) Filed: Jul. 13, 2023

(65) Prior Publication Data
US 2023/0360514 A1 Nov. 9, 2023

Related U.S. Application Data

(63) Continuation of application No. 17/679,701, filed on Feb. 24, 2022, now Pat. No. 11,741,818.

(60) Provisional application No. 63/163,458, filed on Mar. 19, 2021.

(51) Int. Cl.
| | |
|---|---|
| *G08B 21/24* | (2006.01) |
| *G01S 1/04* | (2006.01) |
| *G16H 40/20* | (2018.01) |
| *H04W 4/80* | (2018.01) |

(52) U.S. Cl.
CPC .......... *G08B 21/245* (2013.01); *G01S 1/047* (2013.01); *G16H 40/20* (2018.01); *H04W 4/80* (2018.02)

(58) Field of Classification Search
CPC ...... G08B 21/245; G01S 1/047; G16H 40/20; H04W 4/80
See application file for complete search history.

(56) References Cited

U.S. PATENT DOCUMENTS

| | | |
|---|---|---|
| 7,375,640 B1 | 5/2008 | Plost |
| 7,898,407 B2 | 3/2011 | Hufton et al. |
| 8,085,155 B2 | 12/2011 | Prodanovich et al. |
| 8,237,558 B2 | 8/2012 | Seyed et al. |
| 8,294,584 B2 | 10/2012 | Plost |
| 8,394,585 B2 | 3/2013 | Dong et al. |

(Continued)

FOREIGN PATENT DOCUMENTS

| | | |
|---|---|---|
| CN | 106154902 B | 8/2019 |
| CN | 110383355 A | 10/2019 |
| WO | 2010026581 A2 | 3/2010 |

OTHER PUBLICATIONS

Extended European Search Report from European Patent Application No. 22160761.7, dated Jul. 27, 2022, 9 pages.

(Continued)

*Primary Examiner* — An T Nguyen
(74) *Attorney, Agent, or Firm* — Lempia Summerfield Katz LLC (57) ABSTRACT

An apparatus for tracking hand hygiene in a bathroom includes at least a radio and a controller. The radio is configured to receive a direct connection probe from a mobile device. The controller is configured to receive sensor data associated with hand hygiene and match the sensor data associated with hand hygiene with an identifier for the mobile device based on the direction connection probe to determine whether a hand hygiene threshold is met.

14 Claims, 7 Drawing Sheets

(56) References Cited

U.S. PATENT DOCUMENTS

| | | | |
|---|---|---|---|
| 8,698,637 B2 | 4/2014 | Raichman | |
| 9,135,805 B2 | 9/2015 | Freedman et al. | |
| 9,483,930 B1 | 11/2016 | Haaland | |
| 9,542,828 B1 | 1/2017 | Haaland | |
| 9,773,402 B2 | 9/2017 | Raichman et al. | |
| 10,223,894 B2 | 3/2019 | Raichman | |
| 10,373,477 B1 | 8/2019 | Bonner et al. | |
| 10,403,121 B2 | 9/2019 | Liu et al. | |
| 10,410,507 B2 | 9/2019 | Pi | |
| 10,490,057 B1* | 11/2019 | Malina | G06Q 30/02 |
| 10,607,471 B2 | 3/2020 | Hood et al. | |
| 10,679,488 B2 | 6/2020 | Liu et al. | |
| 10,748,410 B2 | 8/2020 | Liu et al. | |
| 2014/0320291 A1* | 10/2014 | De Luca | G08B 21/245 |
| | | | 340/573.1 |
| 2015/0035678 A1 | 2/2015 | Long | |
| 2015/0216369 A1* | 8/2015 | Hamilton | G08B 21/245 |
| | | | 222/23 |
| 2016/0100275 A1* | 4/2016 | Viswanadham | H04W 4/21 |
| | | | 455/41.2 |
| 2018/0122214 A1 | 5/2018 | Freedman | |
| 2018/0151054 A1* | 5/2018 | Pi | G08B 21/245 |
| 2018/0293873 A1* | 10/2018 | Liu | G16H 40/20 |
| 2018/0308340 A1 | 10/2018 | Thiyagarajah et al. | |
| 2019/0001006 A1 | 1/2019 | Rodenbeck et al. | |
| 2019/0147731 A1* | 5/2019 | Herdt | A47K 5/1217 |
| | | | 340/573.1 |
| 2019/0314843 A1 | 10/2019 | Nour-omid et al. | |
| 2019/0378395 A1 | 12/2019 | Pi | |
| 2020/0074836 A1* | 3/2020 | Kolavennu | G06V 40/28 |
| 2020/0302775 A1 | 9/2020 | Liu et al. | |
| 2021/0287520 A1* | 9/2021 | Maeda | A61H 35/00 |
| 2021/0398416 A1* | 12/2021 | Gupta | G06V 40/28 |
| 2022/0157152 A1* | 5/2022 | Broyden | G07C 3/00 |
| 2022/0301413 A1* | 9/2022 | Sinha | G01S 1/047 |

OTHER PUBLICATIONS

Hama et al., "Hand-Hygiene Activity Classification with Accelerometers", IPSJ SIG Technical Reports 2008-CVIM-164, Aug. 2008, pp. 239-244; Abstract in English.

Chinese Office Action from Chinese Patent Application No. 202210269821.X, dated Feb. 15, 2025, 17 pages. (including English summary).

* cited by examiner

SYSTEMS AND METHOD FOR CLOSED LOOP TRACKING OF HAND HYGIENE COMPLIANCE

CROSS-REFERENCE TO RELATED APPLICATIONS

This application claims priority benefit to U.S. Non-Provisional Utility application Ser. No. 17/679,701 filed on Feb. 24, 2022, which claims priority to and the benefit of U.S. Provisional Utility Application Ser. No. 63/163,458 filed on Mar. 19, 2021, and the entire disclosure of each is hereby incorporated by reference.

FIELD

The present application relates generally to the detection of hand hygiene and closed loop tracking of compliance with hand hygiene practices within a particular location.

BACKGROUND

Recent events have focused new attention on infections and the efficacy of hand washing for the prevention of spreading infection. Hospital-acquired infections (HAI) are a persistent problem in the healthcare industry that costs thousands of lives and billions of dollars annually. Improper hand hygiene is one of the biggest factors contributing to HAI. The World Health Organization has issued guidelines to ensure proper hand-hygiene that include recommend hand washing practices to mitigate the spread of infection.

However, education on hand hygiene cannot ensure compliance. Tracking systems that track the hand hygiene practices of individuals can improve compliance and reduce the spread of infections.

BRIEF DESCRIPTION OF THE DRAWINGS

Exemplary embodiments are described herein with reference to the following drawings, according to an exemplary embodiment.

DETAILED DESCRIPTION

Wearable devices, or mobile devices in general, may be used to identify and notify if impacted people, especially healthcare professionals are following the recommended hand hygiene protocols. Such devices may include accelerometers and gyroscopes to detect the duration and motion of hand washing of individuals. Such devices may include wireless protocol (e.g., Bluetooth) chipsets on the wearables and certain risk-zones may include beacons to determine when people should wash their hands.

Figure 1:
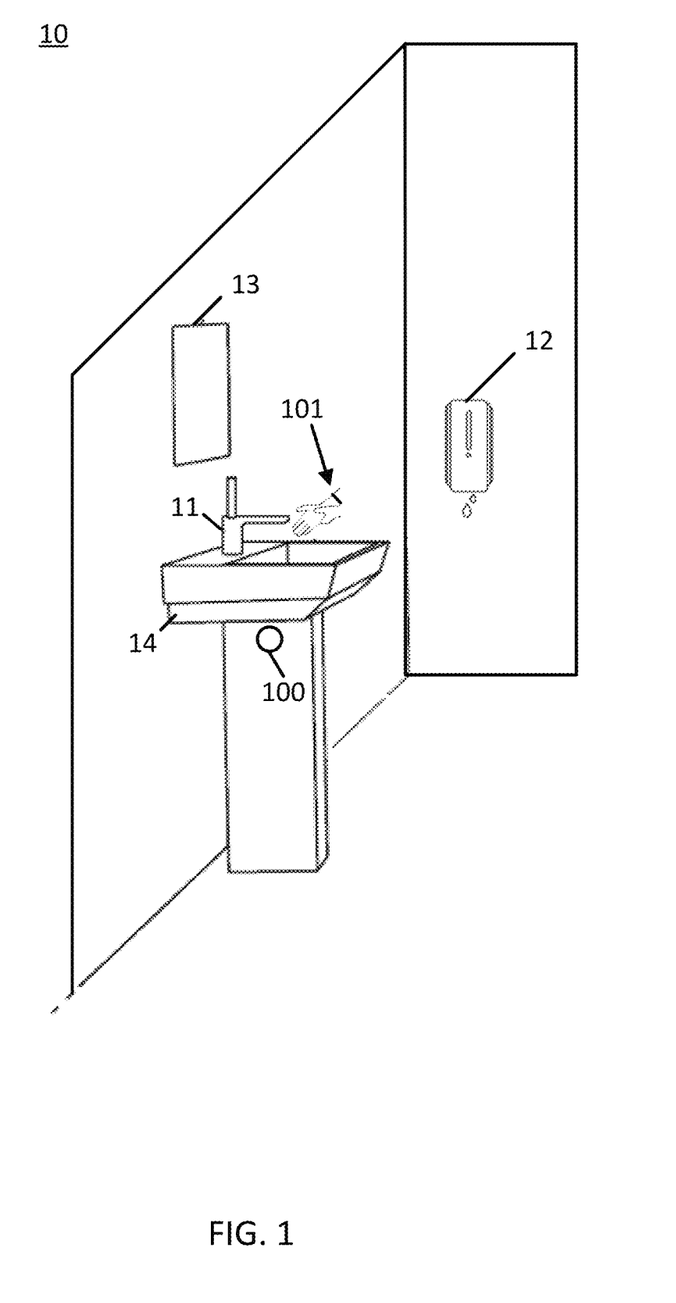
FIG. 1 illustrates a first example bathroom setting for various embodiments of hand hygiene tracking.

In some scenarios, when presence near the hand washing station is used, it is possible for the user to skip hand washing. Further when, the duration and motion of hand washing is detected, a user may pretend to wash their hands after entering a risk-zone and they may be determined as compliant even though the hand hygiene protocol has not been followed. These devices could be improved through tracking the use of soap and water in the handwashing process. In some examples, agents besides soap and water, such as sanitizer may be tracked. The following embodiments incorporate usage sensors in the implements of handwashing, including faucets, soap dispensers, disinfectant dispensers, air dryers, paper towel dispensers, and others FIG. 1 illustrates a first example bathroom or lavatory setting 10 for various embodiments of hand hygiene tracking. The lavatory setting 10 may be included in a patient's room in a hospital or other health care facility. The lavatory setting 10 may be included in a surgical area (e.g., a lavatory or scrub sink adjacent to an operating room). The lavatory setting 10 may be included in a home or business. The lavatory setting 10 may be a physical gateway between a public area that is hygienically unsecured or uncontrolled, such as a public waiting area and a hygienically secured or controlled area such as a patient's room (e.g., operating room, pandemic designated room) or operating room. In other words the lavatory setting 10 may include at least two walls or doorways where one wall or doorway separates the lavatory setting 10 from the hygienically unsecured area and another wall or doorway separates the lavatory setting 10 from the hygienically secured area. For example, a doctor may enter the lavatory setting 10, from the hygienically unsecured area (general hospital area), to the space where hand hygiene is tracked, and the doctor may leave the lavatory setting 10 into the hygienically secured area (operating room), after one or more hygiene thresholds are met.

A hand hygiene controller 100 may perform a variety of functions related to hand hygiene and the tracking and monitoring thereof, according to the following embodiments. Additional, different, or fewer components may be included.

The example lavatory setting 10 may include any combination of a sink including a basin 14 and a faucet 11, a soap dispenser 12, and a mirror 13. At least one device in the lavatory setting 10 includes a flow related sensor. Data from the flow sensor allows the hand hygiene controller 100 to monitor handwashing practices. In some examples, the faucet 11 or plumbing leading to the faucet 11 includes a flow sensor that measures the flow of water to the faucet 11. In some examples, the soap dispenser 12 includes a flow sensor that measures the flow of soap dispensed. While illustrated as a wall hung soap dispenser, the soap dispenser 12 may alternatively be mounted on the deck, near the basin, incorporated in the basin, or incorporated into the faucet 11. Additional, different, or fewer components may be included.

The flow sensor may be a pressure sensor, ultrasonic sensor, or light sensor. The light sensor may measure the quantity of water that passes a light beam. The pressure sensor may detect the pressure of water inside a hose, a pipe or other plumbing device. The flow sensor may include two or more pressure sensors located at different places along the faucet 11 or plumping leading to the faucet 11. For example, the flow sensor may include a downstream pressure sensor and an upstream pressure sensor. The hand hygiene controller 100 may calculate the flow between the downstream pressure sensor and the upstream pressure sensor based on pressure measurements made by the respective sensors. The change in pressure may be proportional to the flow rate. The calculated flow may also be proportional to the size of the pipe (e.g., the square of the radius). The calculated flow rate may also depend on viscosity.

The ultrasonic sensor generates an ultrasonic wave that travels through the flow of water and is received at a received. Based on the received ultrasonic wave the volume and/or speed of the flow of water is detected. The sensor may be paired with two polished surface that reflects the ultrasonic wave or the light beam on the opposite side of the flow of water and returns the ultrasonic wave or the light beam to the sensor.

As an alternative to the flow sensor, the flow of water and/or soap may be determined according to the operation of a valve. For example, a solenoid may open and close the flow of water or soap. The hand hygiene controller 100 may control the solenoid to actuate in order to open or close the valve, for example, using an open command (e.g., energize the solenoid) and a close command (e.g., de-energize the solenoid). The open command, or turning on the faucet 11 or soap dispenser 12, may be generated in response to a user command. The user command may be a mechanical button (e.g., move the faucet handle or knob) or a motion sensor (e.g., wave an arm or hand in front of the motion sensor). The hand hygiene controller 100 may calculate a flow rate for the faucet 11 or the soap dispenser 12 using a time difference between the open command and the closed command. The hand hygiene controller 100 may include a lookup table that relates the amount of time that the faucet 11 is on to flow amounts. In some examples, the time between the open and close commands is a predetermined time period, and in turn, the flow rate for one operation of the faucet 11 or the soap dispenser 12 is a set amount.

In any of these examples, the flow of sanitizer may be tracked as an alternative or addition to the flow of water and/or soap. The flow of sanitizer may be detected by any of the sensors described herein.

The hand hygiene controller 100 may receive the flow sensor data and determine hand hygiene compliance. The hand hygiene controller 100 may determine whether a handwashing event has met one or more handwashing thresholds. The handwashing threshold may be a time of water flow for the faucet 11. The handwashing threshold may be a time duration or volumetric total of soap dispensed for the soap dispenser 12. The handwashing threshold may be a sequence for the faucet 11 and the soap dispenser 12. An example sequence may be water for a particular duration or amount then soap for a particular duration. An example sequence may be soap then water. An example sequence may be water for a particular duration or amount then soap then water for a particular duration. Additional water/soap usage sequences are described below. In addition, sanitizer may be in the sequence.

A wearable device 101, or another type of mobile device such as a smart phone, may detect the movements of the user. The mobile device may include one or more inertial measurement unit sensors such as an accelerometer or a gyroscope. As the user moves with the mobile device, the sensor may generate one or more vectors that represent the acceleration or position of the user. The vectors may be compared to one or more handwashing patterns by the hand hygiene controller 100. The thresholds may require that the hands are moving with a particular change in position or a particular acceleration consistent with handwashing. Additional handwashing patterns are described below.

The hand hygiene controller 100 may trigger the comparison of the handwashing pattern and/or the water/soap usage sequence based on an external event. In one example, the external event is the entry of the user into the lavatory setting 10. The external event may be indicated by opening the door, detection of a motion detector in the lavatory setting 10, or a sensor provided behind or otherwise associated with the mirror 13. The external event may be indicated by "badging" into the lavatory setting 10. That is the user may place a badge or other device such as a radio frequency identification (RFID) tag or near field communication (NFC) at or near a plate or other reading sensor that triggers a latch or unlocks the door the lavatory setting 10, or otherwise checks the user into the lavatory setting 10.

In another example, explained in detail below, the wearable device 101 (e.g., mobile device) may be detected by the hand hygiene controller 100 using a wireless transmitter. In some examples, the wireless transmitter (e.g., Bluetooth beacon) is incorporated in the hand hygiene controller 100 and in other examples, the wireless transmitter is a separate device. The hand hygiene controller 100 may be incorporated into any of the example hand hygiene dispensers (e.g., the faucet 11) or other examples described herein. A beacon may include a transceiver or receiver configured for a particular protocol and/or frequency range. The beacon may include a wireless communication circuit that filters an identifier from a probe message (i.e., removes the payload of the probe messages).

In some embodiments, the hand hygiene controller 100, flow related sensor, and the wireless transmitter are external to the faucet 11. The faucet 11 may include one or mechanical valves operated manually. Upstream of the mechanical valve, the flow related sensor may be installed in-line with the faucet 11. According to any of the procedures described herein, the hand hygiene controller 100 may identify a mobile device for a user in response to communication with the mobile device and associate a water flow measured by the external flow related sensor. The hand hygiene controller 100 determines whether a hand hygiene threshold is met based on the water flow and generates a message associated with the identified user or mobile device.

Figure 2:
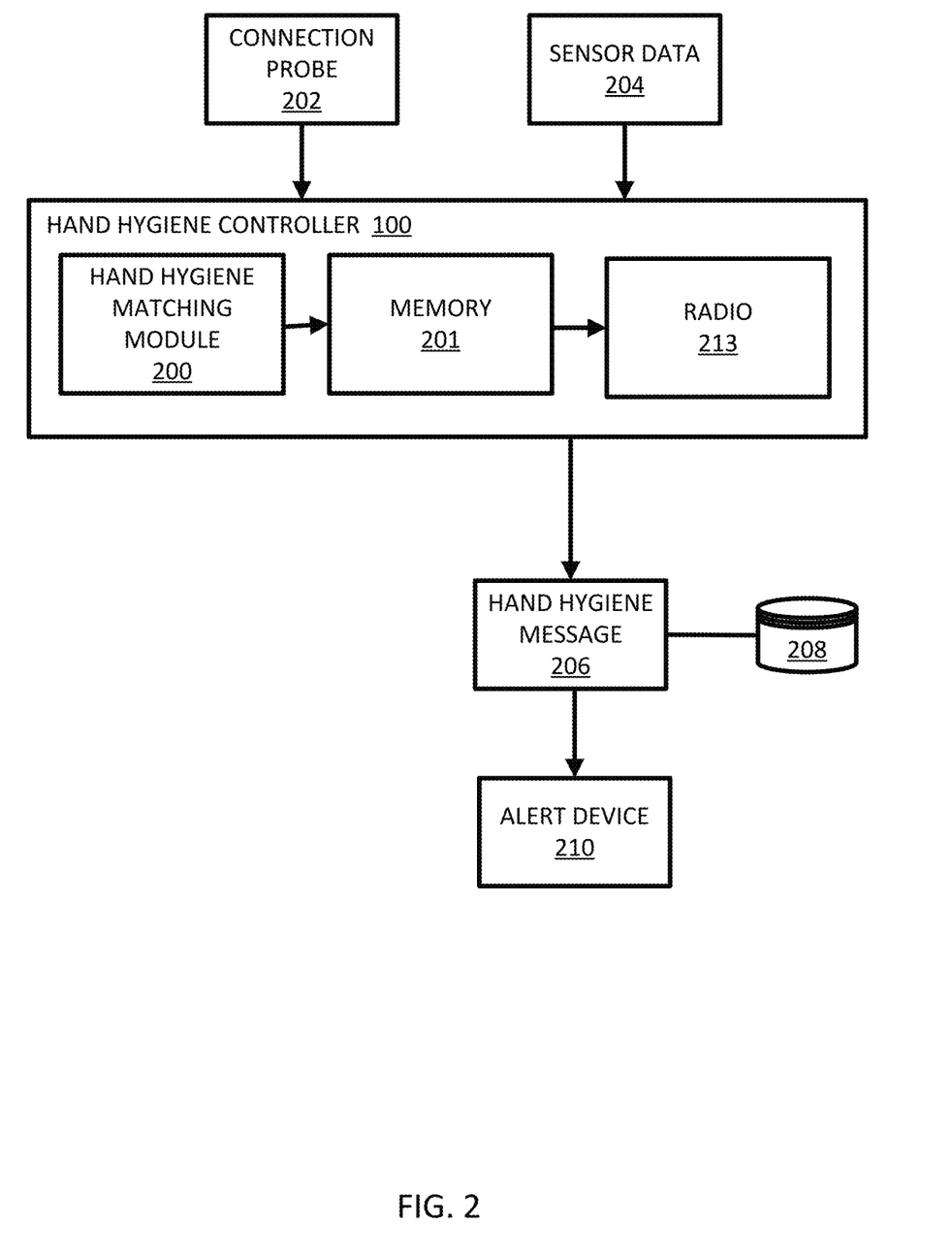
FIG. 2 illustrates an example diagram for hand hygiene tracking.

FIG. 2 illustrates an example block diagram for hand hygiene tracking. The hand hygiene controller 100 includes a hand hygiene matching module 200, a memory 201, a radio 213, and optionally, one or more additional components. The hand hygiene controller 100 may receive data from one or more other device such as the connection probe 202 from the wearable device 101 or other mobile device and/or the senor data 204 from the flow sensor and/or another sensor. Additional, different, or fewer components may be included.

The radio 213 is configured to receive a direct connection probe from the mobile device (i.e., a radio of the mobile device). The direction connection probe may be transmitted using radio frequency communication over a wireless network. Example wireless networks include cellular networks, the family of protocols known as WiFi or IEEE 802.11, the family of protocols known as Bluetooth, near field communication, or another protocol.

The Bluetooth protocol, or another ad hoc network, may allow for the direct connection probe without user intervention. For example, a Bluetooth transceiver may transmit or broadcast a packet of information that advertising the existence of the Bluetooth transceiver as available for an ad hoc connection. The existence of the direction connection probe, or put another way, the ability of the radio 213 to receive the direction connection probe from the mobile device, indicates that the mobile device is in proximity to the lavatory setting 10.

Other qualifying tests may be used. For example, the hand hygiene controller 100 may determine the signal strength from the direct connection probe. If the direct connection probe has a signal strength below a threshold signal strength, the direct connection probe is dismissed (e.g., omitted or deleted). If the direct connection probe has a signal strength above the threshold signal strength, the direct connection prove is further analyzed. In another example, the hand hygiene controller 100 may monitor for multiple probes from the same mobile device. The hand hygiene controller 100 may determine that the mobile device is in proximity to the lavatory setting if a predetermined number of probes are received in a predetermined amount of time.

The direction connection probe may include an identifier for the Bluetooth transceiver and/or the sending mobile device. The hand hygiene matching module 200 receives the direct connection probe from the radio 213, and analyzes the direct connection probe for any identifiers, and identifies an identifier for the mobile device from the direction connection probe.

In addition or as an alternative to ad hoc network probes, the hand hygiene controller 100 may be coupled with a heat sensor. For example, a heat sensor in the ceiling or mounted on a wall of the room may detect the presences of individuals and in proximity to the handwashing station. The heat sensor may identify a heat signature for a particular individual. An identity with the heat signature may be matched with any of the hand hygiene thresholds and user behavior described herein.

As described in various examples herein, the hand hygiene matching module 200 determines whether the current user has met one more hand hygiene thresholds. The hand hygiene matching module 200 may receive sensor data from the faucet 11 or soap dispenser 12 indicated a duration and/or volume of water or soap that has been dispensed. The hand hygiene matching module 200 may compare the duration or volume to the one or more hand hygiene thresholds. When the duration or volume exceeds the hand hygiene threshold, the hand hygiene matching module 200 may determine that the user has met the threshold.

The hand hygiene matching module 200 may receive sensor data from the wearable device 101 to indicate the handwashing movement of the user. The hand hygiene matching module 200 may compare the movement of the user to one or more handwashing patterns. When the movements are a match to a handwashing, the hand hygiene matching module 200 may determine that the user has met one or more hand hygiene thresholds.

The hand hygiene matching module 200 may also compare sensor data from both the wearable device 101 and the faucet 11 and/or the soap dispenser 12 to determine whether the hand hygiene thresholds have been met.

The hand hygiene matching module 200 may is configured to generate a message 206 indicative of whether the hand hygiene threshold is met. The hand hygiene matching module 200 may store data indicative of whether the hand hygiene threshold is met in the memory 201. The message may be transmitted to a database 208. The database 208 or the memory 201 may store the result of the hand hygiene threshold comparison with an identifier for the user. The identifier may have been accessed from the direction connection probe. The identifier may be a media access control (MAC) address or other hardware address for the mobile device. The identifier may be an internet protocol (IP) or other network address for the mobile device. The identifier may be a username, an employee identification number, a student identification number, a social security number, or another number. The identifier may be associated with a name. The identifier may be associated with a type of employee or individual. For example, in a medical setting, the type me be a doctor, a nurse, a patient, and a visitor.

The hand hygiene matching module 200 may send the message 206 indicative of whether the hand hygiene threshold is met to an alert device. The alert device 210 may be a display, an audible alarm, a video, a light emitting diode (LED), a vibration device, a light, an overlay or projection on mirror 13, or another indicator. The alert device 210 may describe a colored light (e.g., green for when the hand hygiene threshold has been met and red for when the hand hygiene threshold has not been met). The alert device 210 may include a recording that indicates whether or not the hand hygiene threshold has been met. The alert device 210 may include a record that instructs the user to "use more water" or "scrub hands vigorously." The alert device 210 may produce a vibration, chime, or flashing light when the hand hygiene threshold has been met. The alert device 210 may be mounted on or integrated with the faucet 11 or the soap dispenser 12.

The alert device 210 may be located outside of the lavatory setting 10. In addition or in the alternative to the alert device 210, the hand hygiene message 206 may trigger a transmission to another device. For example, the handwashing protocol of users (e.g., employees) may be monitored from another location.

In another example, the message 206 and/or the alert device 210 may be associated with an egress or door from the lavatory setting 10. The alert device 210 may indicate that to exit the lavatory setting when the hand hygiene threshold has been met. The alert device 210 may include a magnetic latch or other mechanism that causes the exit to the lavatory setting 10 to open when the hand hygiene threshold has been met. In some examples, the lavatory setting 10 may include multiple doorways. At least one doorway may lead to a hygienically secured area and at least one doorway may lead to a hygienically unsecured area. The doorway to unsecured area may remain unlocked at all times. The doorway to the secured area may only be unlocked in response to the hand hygiene threshold being met. That is, the hand hygiene message 206 may be sent to a lock on the door. For example, the user may be prevented from egresses the lavatory setting 10 to a protected environment such as an operating room or a patient's room. That is, an electronic lock on at least door may remain locked until one or more hand hygiene thresholds have been met and the electronic lock is causes to unlock in response to the message 206 for hand hygiene.

Figure 3:
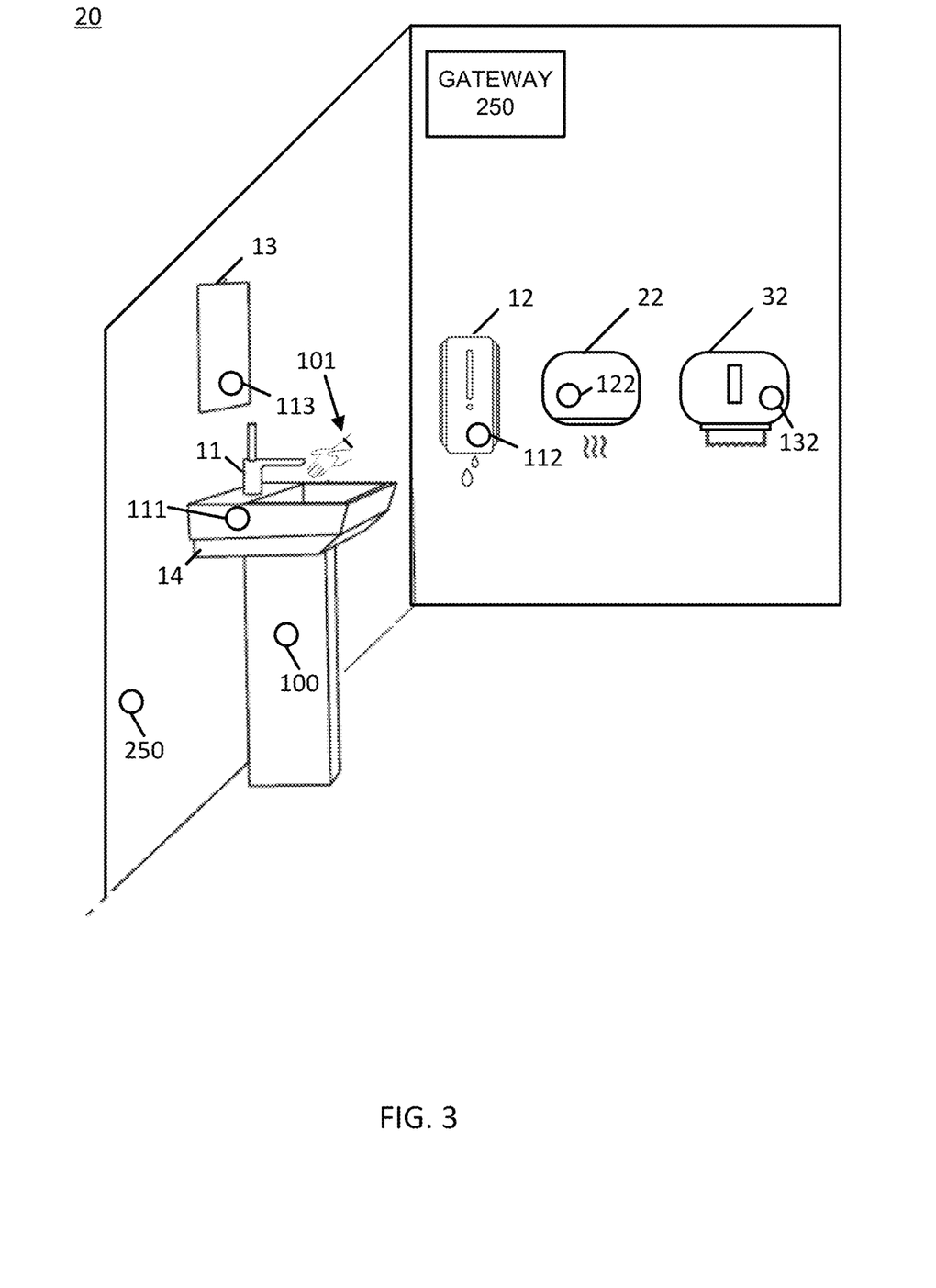
FIG. 3 illustrates a second example bathroom setting for various embodiments of hand hygiene tracking.

FIG. 3 illustrates a second example bathroom setting 20 for various embodiments of hand hygiene tracking. The example lavatory setting 20 may include any combination of a sink including a basin 14 and a faucet 11, a soap dispenser 12, a mirror 13, an air dryer 22, and a paper towel dispenser 32. At least one device in the lavatory setting 20 includes a flow related sensor. Examples include a water flow sensor 111 associated with the faucet 11, a soap sensor 112 associated with the soap dispenser 12, an air flow sensor 122 associated with the air dryer 22, and a paper towel sensor 132 associated with the paper towel dispenser 32. Any of these devices may also include the hand hygiene controller 100, or a distributed set of hand hygiene controller, that tracks hand hygiene according to any of the examples herein. Any of these devices may be considered a hand hygiene dispensers to the extent a consumable is dispensed such as water, soap, air, paper, etc. Any of the hand hygiene dispensers may receive the direct connection probe for identification of nearby users or mobile devices from the direction connection probe.

Data from the flow sensor allows the hand hygiene controller 100 to monitor handwashing practices. In some examples, the faucet 11 or plumbing leading to the faucet 11 includes the flow sensor 111 that measures the flow of water to the faucet 11. In some examples, the soap dispenser 12 includes the soap sensor 112 that measures the flow of soap dispensed. The air flow sensor 122 in the air dryer 22 may detect the amount of time that the air dryer is operated. The sensor 132 in the paper towel dispenser 32 may determine when paper towels have been distributed. Each of the sensors may communicate with a gateway 250 or another network device that communicates with a central controller or a central database (e.g., in the cloud). The central controller or central database may track multiple bathroom settings, for example, multiple rooms in a hospital or other facilities or multiple facilities in a geographic area.

In one example, the mirror may include a video camera 113. The video camera 113 may be mounted elsewhere. The video collected by the video camera 113 may be analyzed to determine whether one or more hand hygiene thresholds have been met.

In one example, the lavatory may include a built in sensor (e.g., camera, infrared, proximity, or another type of sensor), along with built in faucet 11 or a built in soap dispenser. The integrated sensor may collect data that is compared to one or more hand hygiene threshold to determine whether the correct handwashing protocol is followed. In one example, water is provided with the faucet 11 until the hand hygiene threshold is met. In another example, water is provided for a predetermined time (e.g., 20 seconds).

Figure 4:
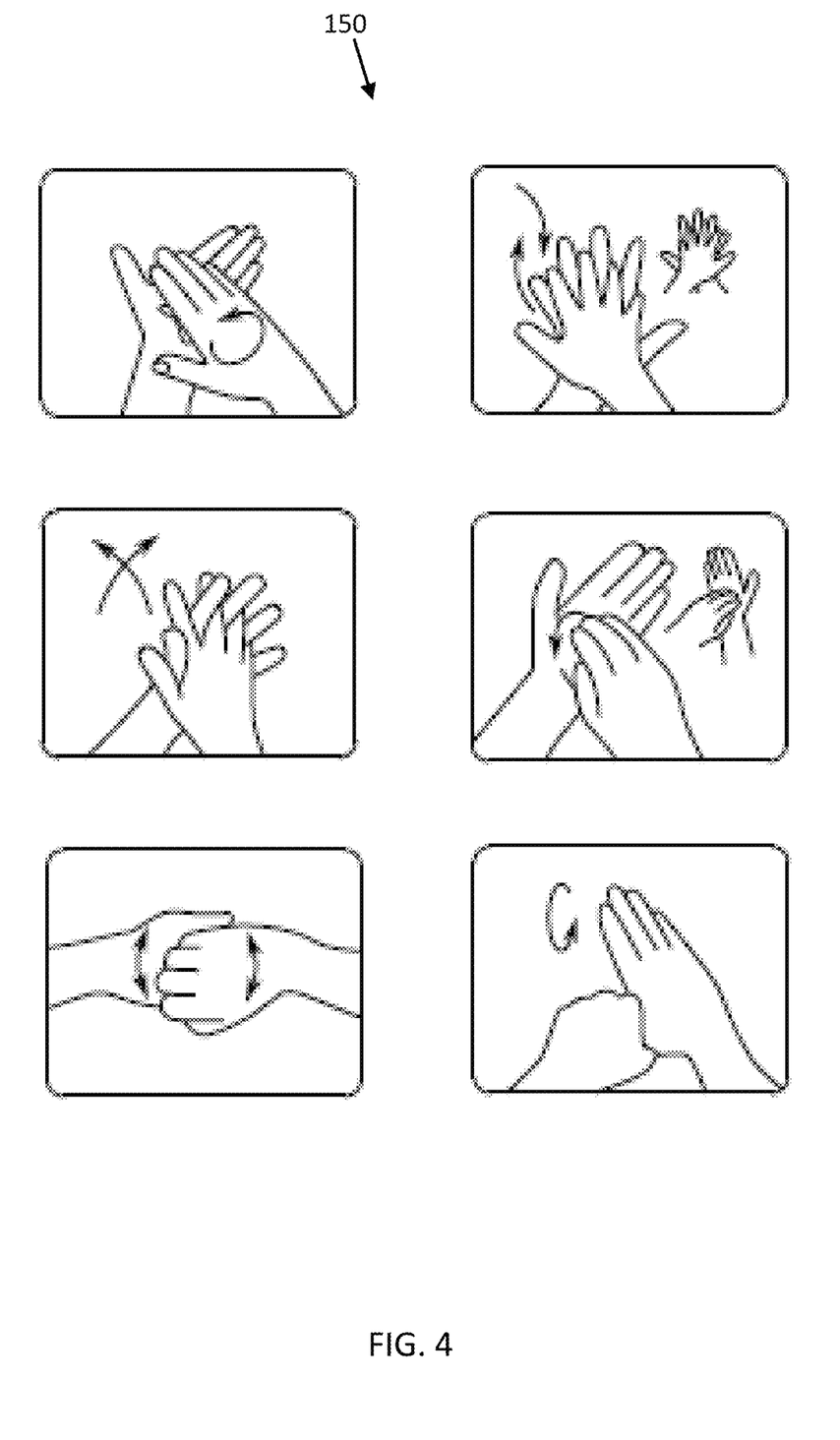
FIG. 4 illustrates example hand movement patterns for hand hygiene.

FIG. 4 illustrates example hand movement patterns 150 for hand hygiene. As illustrated, the patterns are images that indicate to a user how to wash hands. These patterns 150 may be displayed (e.g., on the mirror 13, the mobile device, or an external display). In addition, underlying one or more of these patterns 150 is a set of vectors stored by the hand hygiene controller 100. The hand hygiene controller 100 may compare the patterns 150 or corresponding set of vectors to the motions of the user detected by the inertial measurement unit or other sensors of the mobile device, or inferred from video.

Different patterns or thresholds for different people or types of people. More stringent or strict patterns may be applied to nurses or doctors, while less strict patterns may be applied to other users. The patterns may be selected based on the type of room that is entered from the bathroom setting. For example, when the bathroom setting is a passageway to an operating room, strict patterns are used.

Figure 5:
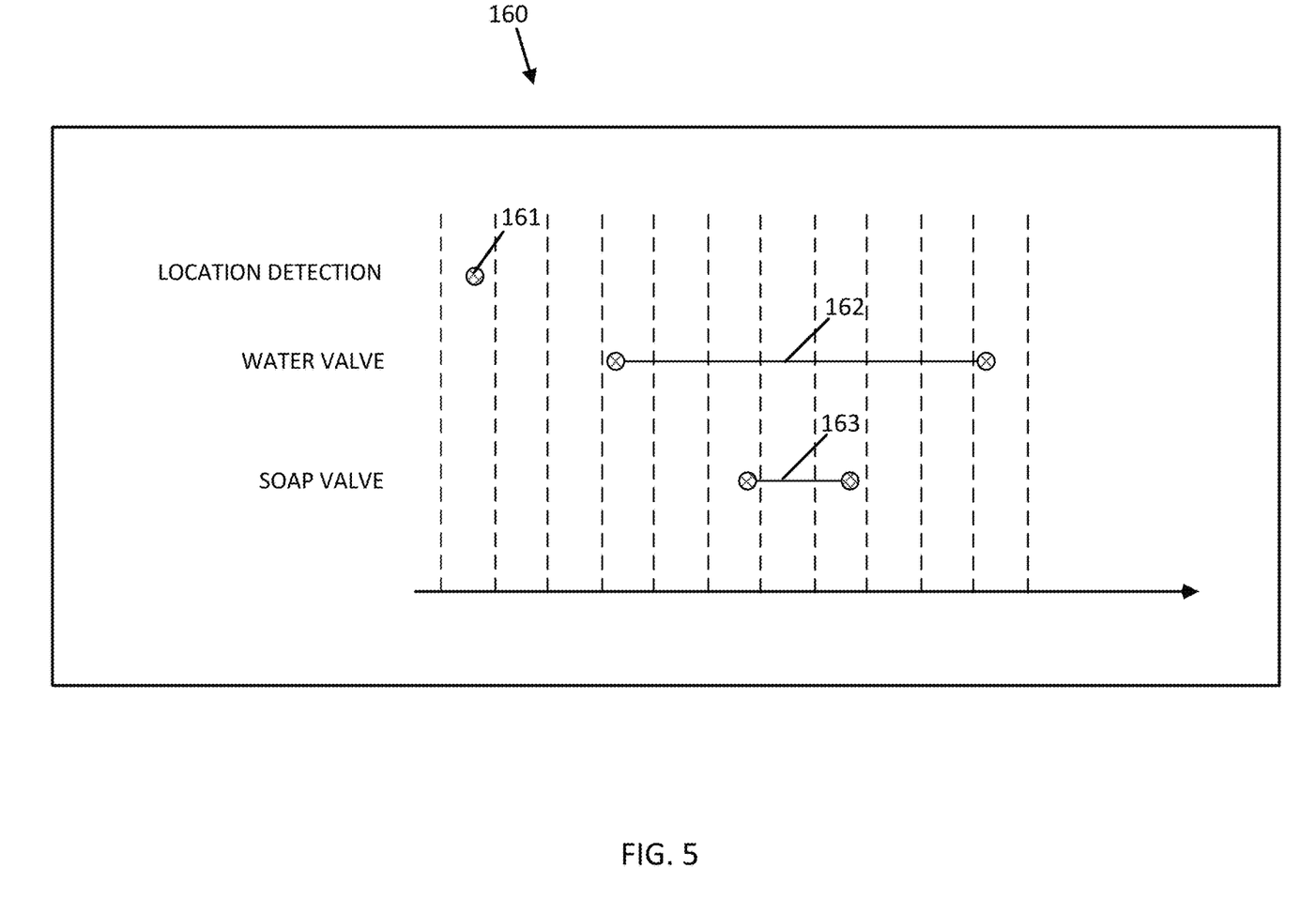
FIG. 5 illustrates example valve patterns for hand hygiene.

FIG. 5 illustrates example valve patterns 160 for hand hygiene. The horizontal axis represents time and provides a visual representation or graph 161 of when data may be received for the location detection or identifier of the mobile device, a visual representation or graph 162 for the detection of the water valve, and a visual representation or graph 163 of the detection of the soap valve.

The hand hygiene matching module 200 may is configured to identify a first timestamp for the direct connection probe and identify a second timestamp for the sensor data associated with hand hygiene. The sensor data is matched to the identifier for mobile device based on a comparison of the first timestamp and the second timestamp.

The example valve patterns illustrate graphically that a particular sequence may be required for the hand hygiene threshold. For example, after location detection is made (e.g., a direct probe connection is received from the mobile device), the hand hygiene controller 100 matches the operation of the water valve with the interval in the pattern, and at some portion during the operation of the water valve, the hand hygiene controller matches the operation of the soap dispenser with the interval in the pattern. A variety of sequences and patterns may be used for the detection of the user, the flow of water, the flow of soap, the flow of air, and/or dispending towels. Other pattern elements are possible.

For example, the hand hygiene matching module 200 determine that location detection is made and subsequently both the operation of the water valve operation of the soap dispenser has been detected. In some examples, the soap dispenser may be detected before the water valve and still match the pattern. In some examples, only the water is detected. In some examples, the water valve and the soap dispenser may be detected simultaneously (e.g., a user may activate water with one hand and soap with the other hand).

Figure 6:
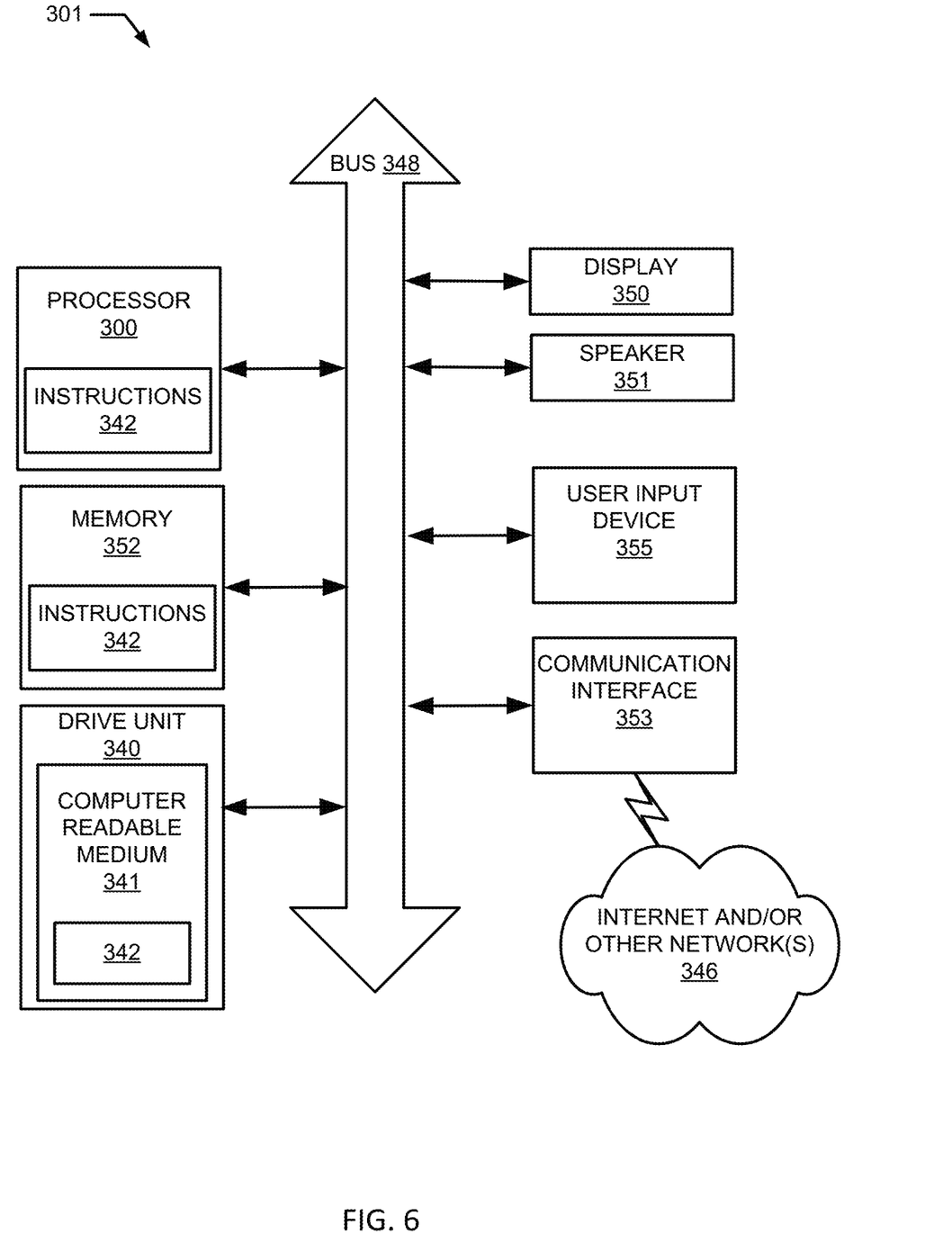
FIG. 6 illustrates a controller for hand hygiene tracking.

FIG. 6 illustrates an example controller 400 for the hand hygiene controller 100 of the hand hygiene system. The controller 400 may include a processor 300, a memory 352, and a communication interface 353 for interfacing with devices or to the internet and/or other networks 346. In addition to the communication interface 353, a sensor interface may be configured to receive data from the sensors described herein. The components of the control system 400 may communicate using bus 348. The control system 400 may be connected to a workstation or another external device (e.g., control panel) and/or a database for receiving user inputs, system characteristics, and any of the values described herein.

Optionally, the control system 400 may include an input device 355 and/or a sensing circuit in communication with any of the sensors. The sensing circuit receives sensor measurements from as described above. The input device 355 may include a touchscreen coupled to or integrated with the mirror, a keyboard, a microphone for voice inputs, a camera for gesture inputs, and/or another mechanism.

Optionally, the control system 400 may include a drive unit 340 for receiving and reading non-transitory computer media 341 having instructions 342. Additional, different, or fewer components may be included. The processor 300 is configured to perform instructions 342 stored in memory 352 for executing the algorithms described herein. A display 350 may be supported by the mirror frame. The display 350 may be combined with the user input device 355.

Figure 7:
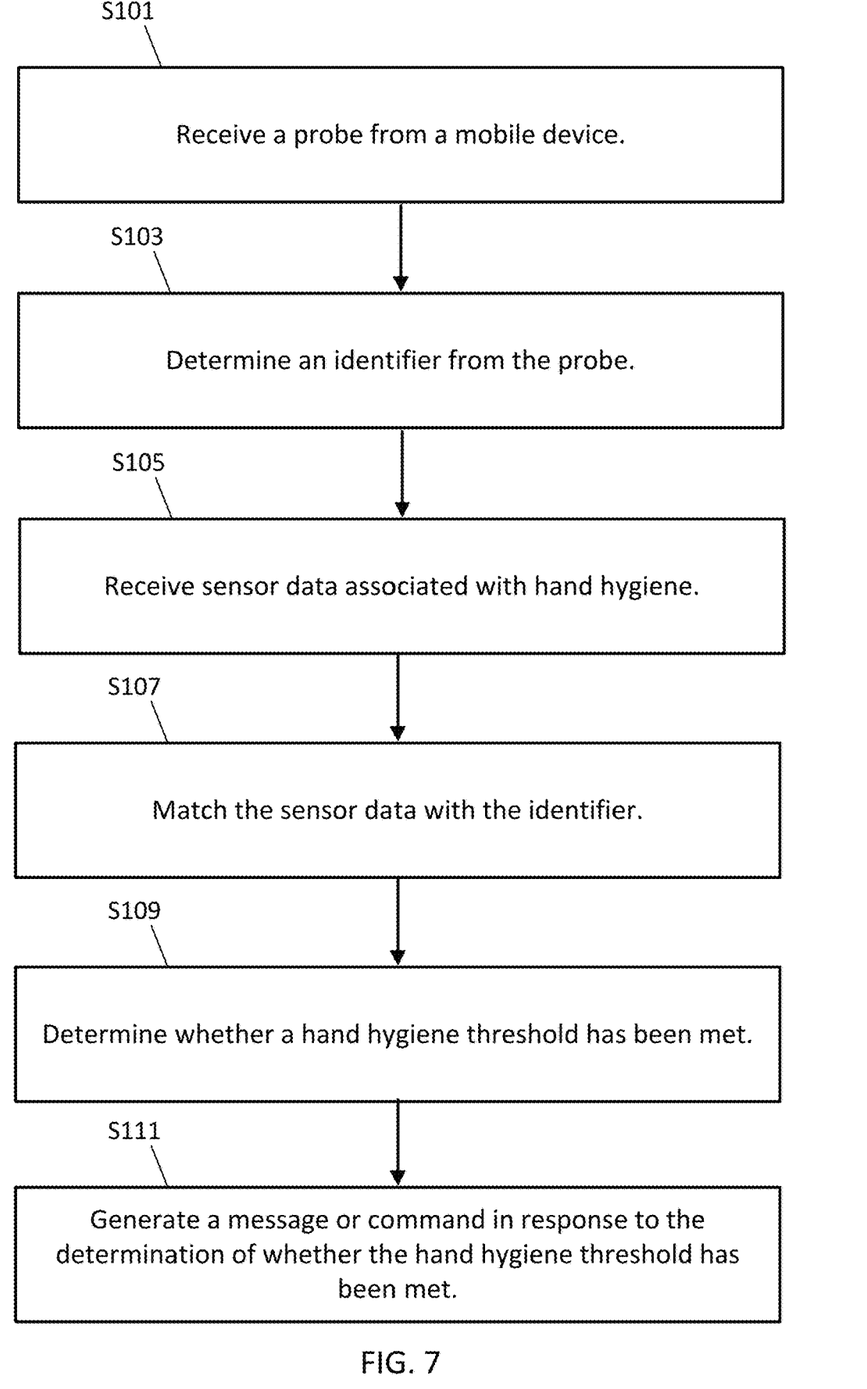
FIG. 7 illustrates a flow chart for the controller of FIG. 6.

FIG. 7 illustrates a flow chart for the control system 400 of the hand hygiene system. The acts of the flow chart may be performed by any combination of the control system 400, the network device or the server. Portions of one or more acts may be performed by the appliance. Additional, different of fewer acts may be included.

At act S101, the controller 400 (e.g., through communication interface 353) receives a direct connection probe from a mobile device. The communication interface 353 may include an antenna or a radio that receives the probe using an ad hoc networking protocol such as Bluetooth. The direct connection probe may be an attempted connection or an advertisement that the mobile device is within range of the controller 400.

At act S103 the controller 400 (e.g., through processor 300) determines an identifier for the mobile device based on the direct connection probe. An address in the probe may be matched through a lookup table to the identifier for a user (e.g., employee). The direct connection probe may include a MAC address or an IP address of the mobile device. The controller 400 may access the lookup table or other paired data from the memory 352 in order to determined which user is indicated by the direct connection probe.

At act S105, the controller 400 (e.g., through processor 300) receives sensor data associated with hand hygiene. The sensor data may be usage information associated with hand hygiene tools. The sensor data may include water flow information for a sink. The sensor data may include soap flow information for a soap dispenser. The sensor data may include flow information for a sanitizer dispenser. The sensor data may be include operation of a towel dispenser or an air dryer.

At act S107, the controller 400 (e.g., through processor 300) matches the sensor data associated with hand hygiene with the identifier for mobile device. The sensor data may be matched with the identifier based on time. For example, when the hand hygiene sensor data is timestamped or received within a certain time range to the timestamp or receipt of the identifier, the two are matched. Example time ranges include 100 milliseconds, 500 milliseconds, and 2 seconds. When the hand hygiene sensor data and identifier are separated in time by more than the threshold time range, the controller 400 may reset (e.g., delete or dismiss the hand hygiene sensor data, the identifier, or both). In some examples, the identifier for the mobile device is matched with the nearest hand hygiene data in time.

At act S109, the controller 400 (e.g., through processor 300) determines whether a hand hygiene threshold is met. The controller 400 may compare the sensor data with one or more patterns or sequences indicative of effective hand washing. The threshold may be received from communication interface 353 from an external device over the network 346. The external device may be a municipality, a central controller, or a user device (e.g., mobile phone). The threshold may be received from user input device 355.

At act S111, the controller 400 (e.g., through processor 300) generates a message or command indicative of whether the hand hygiene threshold is met. The message may be presented by display 350 or by the mobile device. The command may instruct another device to generate an indicator (e.g., light, audio, vibration). The command may instruct a door to unlock. In addition, the controller 400 may store satisfaction of the hand hygiene threshold in memory 352. For example, the controller 400 may set a flag or other alphanumeric value in a table as data indicative of satisfaction of the hand hygiene threshold in association with the identifier for the mobile device or the direct connection probe. The data indicative of satisfaction of the hygiene threshold may be associated with the lavatory setting 10 or a particular lavatory.

The system for hand hygiene may include an available bathroom indicator. In some instances consumables may be missing (e.g., no soap, no paper towels) or a device may be malfunctioning (e.g., no water flow or no air flow). In this instance, the controller 400 may select a nearest working lavatory and direct the user (e.g., with location or directions) using the display 350. The controller 400 may identify the nearest working lavatory as a lavatory that has had a recent satisfaction of one or more hand hygiene thresholds.

The data indicative of satisfaction of the hygiene threshold may be stored across time periods. For example, the data may be tracked for the user (e.g., identifier of mobile device) or for the lavatory setting 10. The controller 400 may determine hygiene performance across the time period. The controller 400 may determine how often the particular user meets the hygiene threshold, which may be the number of times the hygiene threshold is met divided by (or in ratio to) the total number of times the user was present in the lavatory setting 10 or any lavatory setting. The controller 400 may determine how often the particular user meets the hygiene threshold in a particular day, week, month or other time period.

The controller 400 may determine how often a group of users meet the hygiene threshold, which may be the number of times the hygiene threshold is met divided by (or in ratio to) the total number of times any of the group of users were present in the lavatory setting 10 or any lavatory setting. The controller 400 may determine how often the group of users meets the hygiene threshold in a particular day, week, month or other time period.

The controller 400 may determine how often all users in the lavatory setting 10 meets the hygiene threshold, which may be the number of times the hygiene threshold is met divided by (or in ratio to) the total number of times any users were present in the lavatory setting 10. The controller 400 may determine how often users of the particular lavatory setting 10 met the hygiene threshold in a particular day, week, month or other time period.

The message may be presented by display 350 or by the mobile device may indicate how the particular user (e.g., the current user) has performed in meeting the hygiene threshold. An example, performance may be 50% compliant or 80% compliant. Similarly, the message may be presented by display 350 or by the mobile device may indicate the cumulative performance for the lavatory setting 10.

Processor 300 may be a general purpose or specific purpose processor, an application specific integrated circuit (ASIC), one or more programmable logic controllers (PLCs), one or more field programmable gate arrays (FPGAs), a group of processing components, or other suitable processing components. Processor 300 is configured to execute computer code or instructions stored in memory 352 or received from other computer readable media (e.g., embedded flash memory, local hard disk storage, local ROM, network storage, a remote server, etc.). The processor 300 may be a single device or combinations of devices, such as associated with a network, distributed processing, or cloud computing.

Memory 352 may include one or more devices (e.g., memory units, memory devices, storage devices, etc.) for storing data and/or computer code for completing and/or facilitating the various processes described in the present disclosure. Memory 352 may include random access memory (RAM), read-only memory (ROM), hard drive storage, temporary storage, non-volatile memory, flash memory, optical memory, or any other suitable memory for storing software objects and/or computer instructions. Memory 352 may include database components, object code components, script components, or any other type of information structure for supporting the various activities and information structures described in the present disclosure. Memory 352 may be communicably connected to processor 300 via a processing circuit and may include computer code for executing (e.g., by processor 300) one or more processes described herein. For example, memory 298 may include graphics, web pages, HTML files, XML files, script code, shower configuration files, or other resources for use in generating graphical user interfaces for display and/or for use in interpreting user interface inputs to make command, control, or communication decisions.

In addition to ingress ports and egress ports, the communication interface 353 may include any operable connection. An operable connection may be one in which signals, physical communications, and/or logical communications may be sent and/or received. An operable connection may include a physical interface, an electrical interface, and/or a data interface. The communication interface 353 may be connected to a network. The network may include wired networks (e.g., Ethernet), wireless networks, or combinations thereof. The wireless network may be a cellular telephone network, an 802.11, 802.16, 802.20, or WiMax network, a Bluetooth pairing of devices, or a Bluetooth mesh network. Further, the network may be a public network, such as the Internet, a private network, such as an intranet, or combinations thereof, and may utilize a variety of networking protocols now available or later developed including, but not limited to TCP/IP based networking protocols.

While the computer-readable medium (e.g., memory 352) is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding, or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored. The computer-readable medium may be non-transitory, which includes all tangible computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

What is claimed is:

1. A method for controlling access to a hygienically secured area, the method comprising:
   identifying a probe from a mobile device;
   determining a signal strength for the probe from the mobile device;
   in response to the determined signal strength being below a threshold signal strength, dismissing the probe;
   in response to the determined signal strength being a above the threshold signal strength, determining an identifier for the mobile device based on the probe;
   receiving sensor data from a flow sensor associated with hand hygiene;
   determining whether a hand hygiene threshold is met based on the sensor data;
   identifying a first timestamp for the probe;
   identifying a second timestamp for the sensor data associated with hand hygiene;
   matching the sensor data associated with hand hygiene with the identifier for mobile device based on a comparison of the first timestamp and the second timestamp; and
   generating a message to unlock a door for the hygienically secured area when the hand hygiene threshold is met.

2. The method of claim 1, wherein the sensor data associated with hand hygiene includes inertial measurement data.

3. The method of claim 1, further comprising:
   receiving the probe at a hygienically unsecured area.

4. The method of claim 3, wherein the hygienically unsecured area is on a first side of the door and the hygienically secured area is on a second side of the door.

5. The method of claim 1, wherein the hygienically secured area is an operating room.

6. The method of claim 1, further comprising:
   storing data indicative of satisfaction of the hand hygiene threshold in memory.

7. The method of claim 1, wherein the sensor data associated with hand hygiene includes valve operation data.

8. The method of claim 1, wherein the probe is received at a beacon associated with an indoor location.

9. The method of claim 6, further comprising: comparing sensor data to one or more predetermined patterns for hand hygiene.

10. The method of claim 1, wherein the sensor data is generated at a faucet.

11. The method of claim 1, wherein the sensor data is generated at a soap dispenser.

12. An apparatus for controlling access to a hygienically secured area, the apparatus comprising:
    an antenna configured to receive a probe from a mobile device; and
    a controller configured to determine a signal strength for the probe from the mobile device, wherein when the determined signal strength is below a threshold signal strength, the probe is dismissed and wherein when the determined signal strength is above the threshold signal strength, the controller is configured to configured to determine whether a hand hygiene threshold is met based on sensor data from a flow sensor, perform a comparison of a first timestamp for the probe from the mobile device to a second timestamp for the sensor data associated with hand hygiene, and generate a message to unlock a door for the hygienically secured area when the hand hygiene threshold is met.

13. The apparatus of claim 12, wherein the sensor data is generated at, a soap dispenser, or a faucet.

14. An apparatus for controlling access to a hygienically secured area, the apparatus comprising:
    a valve configured to open a flow of water, soap, or disinfectant;
    a radio configured to receive a direct connection probe associated with a first timestamp from a mobile device;
    a flow sensor configured to collect sensor data for the flow of water, soap, or disinfectant associated with a second timestamp for operation of the valve; and
    a controller configured to determine a signal strength for the probe from the mobile device, wherein when the determined signal strength is below a threshold signal strength, the probe is dismissed and wherein when the determined signal strength is above the threshold signal strength, the controller is configured to receive the sensor data for the valve and match the sensor data with an identifier for the mobile device based on a comparison of the first timestamp to the second timestamp to unlock the hygienically secured area.

* * * * *